(12) United States Patent
Hageman et al.

(10) Patent No.: US 6,964,978 B2
(45) Date of Patent: Nov. 15, 2005

(54) SOLID-STATE FORM OF CELECOXIB HAVING ENHANCED BIOAVAILABILITY

(75) Inventors: Michael J. Hageman, Portage, MI (US); Xiaorong He, Kalamazoo, MI (US); Tugrul T. Kararli, Skokie, IL (US); Lesley A. Mackin, Evanston, IL (US); Patricia J. Miyake, Tower Lakes, IL (US); Brian R. Rohrs, Scotts, MI (US); Kevin J. Stefanski, Kalamazoo, MI (US)

(73) Assignee: Pharmacia Corporation, St. Louis, MO (US)

( * ) Notice: Subject to any disclaimer, the term of this patent is extended or adjusted under 35 U.S.C. 154(b) by 45 days.

(21) Appl. No.: 09/730,663

(22) Filed: Dec. 6, 2000

(65) Prior Publication Data

US 2002/0006951 A1 Jan. 17, 2002

Related U.S. Application Data

(60) Provisional application No. 60/169,856, filed on Dec. 9, 1999.

(51) Int. Cl.[7] ...................... A61K 31/415; C07D 231/10
(52) U.S. Cl. ................ 514/406; 548/356.1; 548/373.1; 548/375.1; 548/376.1
(58) Field of Search ........................... 548/373.1, 375.1, 548/376.1, 356.1, 377.1; 514/406

(56) References Cited

U.S. PATENT DOCUMENTS

| | | | | |
|---|---|---|---|---|
| 5,466,823 | A | | 11/1995 | Talley et al. ............. 548/377.1 |
| 5,892,053 | A | | 4/1999 | Zhi et al. ................. 548/377.1 |
| 6,248,745 | B1 | * | 6/2001 | Hamley et al. ............. 514/259 |
| 6,384,034 | B2 | * | 5/2002 | Simitchieva et al. ....... 514/252 |

FOREIGN PATENT DOCUMENTS

| | | | |
|---|---|---|---|
| EP | 0 147 171 | 7/1985 | ......... C07D/401/12 |
| WO | 98/19708 | 5/1998 | |
| WO | WO 98/43980 | 10/1998 | ......... C07D/501/34 |
| WO | WO 00/32189 | 6/2000 | ......... A61K/31/415 |
| WO | WO 00/42021 | 7/2000 | ......... C07D/231/12 |
| WO | WO 00/66562 | 11/2000 | ......... C07D/231/12 |
| WO | WO 01/15664 | 3/2001 | ............ A61K/9/00 |

OTHER PUBLICATIONS

Stavchansky et al: Bioavailability in Tablet Technology. In Pharmaceutical dosage forms, by Marcel Dekker, Inc. p 349–472, 1990.*

* cited by examiner

*Primary Examiner*—Golam M M Shameem
(74) *Attorney, Agent, or Firm*—Patricia K. Fitzsimmons; Charles Ashbrook

(57) ABSTRACT

The selective cyclooxygenase-2 inhibitory drug celecoxib is provided in amorphous form. Also provided is a celecoxib drug substance wherein the celecoxib is present, in at least a detectable amount, as amorphous celecoxib. Also provided is a celecoxib-crystallization inhibitor composite comprising particles of amorphous celecoxib or a celecoxib drug substance of the invention in intimate association with one or more crystallization inhibitors, for example polymers. Also provided is a pharmaceutical composition comprising such a celecoxib-crystallization inhibitor composite and one or more excipients. Also provided are processes for preparing amorphous celecoxib, a celecoxib drug substance of the invention, a celecoxib-crystallization inhibitor composite of the invention, and a pharmaceutical composition of the invention. Also provided is a method of treating a medical condition or disorder in a subject where treatment with a cyclooxygenase-2 inhibitor is indicated, comprising administering, for example orally, a composition of the invention in a therapeutically effective amount.

4 Claims, 5 Drawing Sheets

SOLID-STATE FORM OF CELECOXIB HAVING ENHANCED BIOAVAILABILITY

This application is a continuation-in-part of a U.S. application Ser. No. 09/728,040 filed on Dec. 1, 2000, and also claims priority of U.S. provisional application Ser. No. 60/169,856 filed on Dec. 9, 1999.

FIELD OF THE INVENTION

The present invention relates to the selective cyclooxygenase-2 inhibitory drug celecoxib and in particular to solid-state forms of that drug, to pharmaceutical compositions comprising such solid-state forms, and to processes for preparing them. The invention further relates to methods of treatment of cyclooxygenase-2 mediated disorders comprising administering such solid-state forms or compositions thereof to a subject, and to use of such solid-state forms in the manufacture of medicaments.

BACKGROUND OF THE INVENTION

Celecoxib, also known as 4-[5-(4-methylphenyl)-3-(trifluoromethyl)-1H-pyrazol-1-yl]benzenesulfonamide (I), the active ingredient of Celebrex® marketed by Pharmacia Corp., has a therapeutically and prophylactically useful selective cyclooxygenase-2 inhibitory effect, and has utility in treatment and prevention of specific cyclooxygenase-2 mediated disorders and of such disorders in general. Celecoxib has the structure:

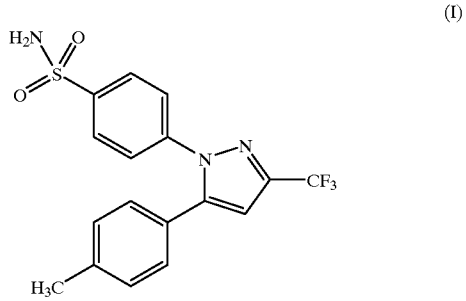

(I)

Processes for preparing celecoxib are set forth in U.S. Pat. No. 5,466,823 to Talley et al. and in U.S. Pat. No. 5,892,053 to Zhi & Newaz, both incorporated herein by reference. Co-assigned International Patent Publication No. WO 00/32189, incorporated herein by reference, discloses that celecoxib has a crystal morphology which tends to form long, cohesive needles. Co-assigned International Patent Publication No. WO 00/42021, incorporated herein by reference, discloses a solvated crystalline form of celecoxib and a method for desolvation of that crystalline form.

A need for new forms of celecoxib, in particular forms suitable for preparing rapid-onset compositions, exists. Rapid-onset drug-delivery systems can provide significant benefits over conventional dosage forms. Generally, rapid-onset preparations provide a short period to therapeutic or prophylactic response compared to conventional immediate-release or sustained-release dosage forms. For example, in treatment of acute pain, a rapid-onset dosage form of celecoxib would be useful to provide fast pain relief.

However, celecoxib presents certain challenges for formulation as a rapid-onset dosage form, particularly as a rapid-onset oral dosage form. For example, celecoxib has very low solubility in aqueous media and therefore is not readily dissolved and dispersed for rapid absorption in the gastrointestinal tract when administered orally, for example in tablet or capsule form. In addition, celecoxib has a relatively high dose requirement further increasing difficulties of providing a sufficient therapeutically effective dose for rapid absorption.

Celecoxib crystals also present formulation difficulties as a result of unique physical and chemical characteristics or mechanical properties such as electrostatic and cohesive properties, low bulk density, low compressibility and poor flow properties. Due at least in part to these properties, celecoxib crystals tend to segregate and agglomerate together during mixing, resulting in a non-uniformly blended composition containing undesirably large, insoluble aggregates of celecoxib. For these and other reasons, therefore, it is difficult to prepare an orally deliverable, rapid-onset composition containing celecoxib that has the desired blend uniformity.

The bioavailability of an orally administered drug, as measured by its entry into systemic circulation in the bloodstream, depends on at least two fundamental processes: drug dissolution in gastrointestinal fluids (in vivo drug release) and subsequent absorption of the dissolved drug. Several factors influence dissolution of a drug from its carrier, including surface area of the drug presented to the dissolution solvent medium, solubility of the drug substance in the solvent medium, and driving forces of the saturation concentration of dissolved materials in the solvent medium.

When the process of in vivo drug release is slower than the process of absorption, absorption is said to be dissolution rate-limited. Since dissolution precedes absorption in the overall process, any change in the drug release or dissolution process will subsequently influence drug absorption. See for example Lieberman et al. (1989), *Pharmaceutical Dosage Forms: Tablets*, Vol. 1, pp. 34–36. Marcel Dekker, New York. It is clear, therefore, that dissolution time determined for a composition is one of the important fundamental characteristics for consideration when evaluating compositions intended for fast-onset delivery, particularly where drug absorption is dissolution rate-limited.

Crystalline solids, due to their highly organized, lattice-like structures, typically require a significant amount of energy for dissolution. The energy required for a drug molecule to escape from a crystal, for example, is greater than is required for the same drug molecule to escape from a non-crystalline, amorphous form. Importantly, however, crystalline drug forms which have been transformed into amorphous forms tend to revert to a steady state of low energy, namely the crystalline form, over time and thus may not have an adequate shelf life. An amorphous form of celecoxib has not hitherto been known in the art.

As indicated hereinbelow, treatment with celecoxib is indicated in a very wide array of cyclooxygenase-2 mediated conditions and disorders. Therefore, if an amorphous form of celecoxib could be prepared, and in particular if a storage-stable composition comprising such an amorphous form of celecoxib could be developed exhibiting enhanced bioavailability, for example through rapid dissolution of the drug, a significant advance would be realized in treatment of cyclooxygenase-2 mediated conditions and disorders, particularly in treatment of acute disorders where early relief from pain or other symptoms is desired.

SUMMARY OF THE INVENTION

Celecoxib provides a more rapid onset of therapeutic effect if, upon oral administration of a composition comprising celecoxib, pharmacokinetic properties are exhibited leading to a greater maximum blood serum concentration ($C_{max}$) and/or a shorter time following the administration to reach that maximum ($T_{max}$). It is contemplated that a greater $C_{max}$ and/or a shorter $T_{max}$ can result from faster dissolution of celecoxib when provided in amorphous form than in crystalline form.

Accordingly, the present invention provides amorphous celecoxib. There is also provided a celecoxib drug substance wherein the celecoxib is present, in at least a detectable amount, as amorphous celecoxib. The term "celecoxib drug substance" as used herein means celecoxib per se as qualified by the context in which the term is used, and can refer to unformulated celecoxib or to celecoxib present as an ingredient of a pharmaceutical composition.

As a further embodiment of the invention, there is provided a celecoxib-crystallization inhibitor composite comprising particles of amorphous celecoxib or a celecoxib drug substance of the invention in intimate association with one or more crystallization inhibitors. The crystallization inhibitors are selected and present in an amount sufficient to substantially reduce conversion of amorphous celecoxib to crystalline celecoxib. Preferred crystallization inhibitors are polymers that form with the celecoxib a celecoxib-polymer composite.

There is also provided a composition comprising a celecoxib-crystallization inhibitor composite, for example a celecoxib-polymer composite, as defined herein. The composition comprises dose units that can be in the form of discrete solid articles such as tablets, caplets, pills, hard or soft capsules, lozenges, sachets or pastilles; alternatively the composition can be in the form of a substantially homogeneous flowable mass, such as a particulate or granular solid or a liquid suspension, for example an imbibable dispersion, from which single dose units are measurably removable.

Also provided are processes for preparing amorphous celecoxib, for preparing a celecoxib drug substance of the invention and for preparing a celecoxib-crystallization inhibitor composite, for example a celecoxib-polymer composite, of the invention.

A preferred process for preparing a celecoxib drug substance of the invention comprises (a) a step of melting celecoxib, for example crystalline celecoxib; and (b) a step of rapidly cooling the resulting melted celecoxib to form a celecoxib drug substance wherein the celecoxib is present, in at least a detectable amount, in amorphous form. Optionally, this process can further comprise (c) a step of grinding the celecoxib drug substance to form a celecoxib powder.

A celecoxib-crystallization inhibitor composite of the invention can be prepared by a process comprising (a) a step of dissolving celecoxib and one or more crystallization inhibitors in a solvent liquid to form a solution; and (b) a step of drying the solution to form a celecoxib-crystallization inhibitor composite wherein the celecoxib and the crystallization inhibitor are in intimate association and wherein a substantial portion of the celecoxib is present in amorphous form. Optionally, this process can further comprise (c) a step of grinding the celecoxib-crystallization inhibitor composite to provide a celecoxib-crystallization inhibitor composite powder.

A celecoxib drug substance or powder thereof, or a celecoxib-crystallization inhibitor composite or powder thereof, prepared according to such processes can be further formulated to provide a pharmaceutical dosage form.

Also provided is a method of treating a medical condition or disorder in a subject where treatment with a cyclooxygenase-2 inhibitor is indicated, comprising administering, for example orally, a composition of the invention in a therapeutically effective amount. Such a method is particularly useful where the medical condition or disorder is accompanied by acute pain.

Other features of this invention will be in part apparent and in part pointed out hereinafter.

DETAILED DESCRIPTION OF THE INVENTION

Amorphous Celecoxib

Figure 1:
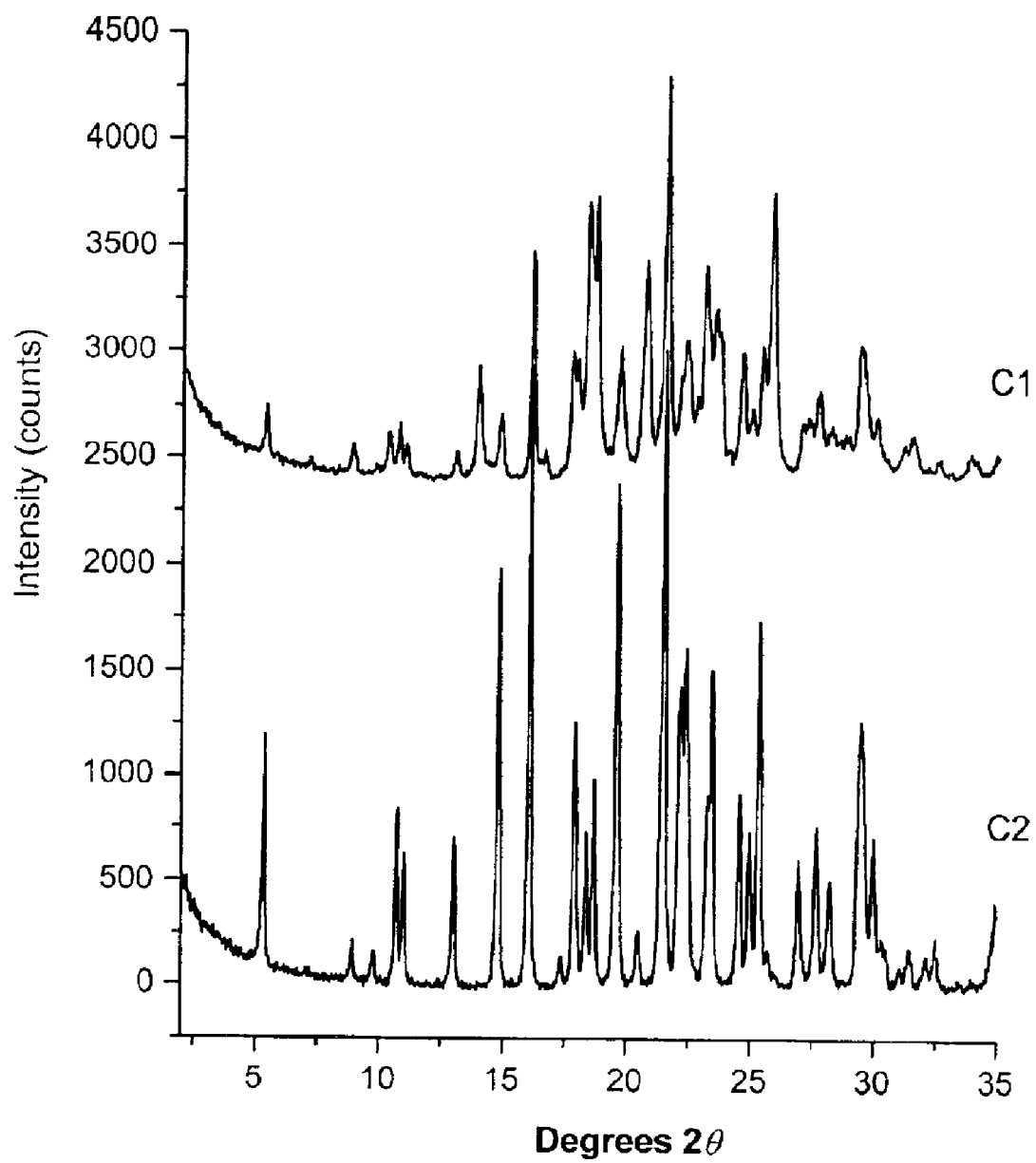
FIG. 1 shows a powder X-ray diffraction profile of a celecoxib drug substance C1 prepared in Example 1, by comparison with crystalline celecoxib C2.

The invention provides a novel amorphous form of celecoxib. The term "amorphous", as used herein, refers to solid-state particles lacking a regular crystalline structure. Without being bound by theory, it is believed that amorphous celecoxib particles require less energy for dissolution than crystalline celecoxib particles of similar dimensions, and that this reduced dissolution energy requirement contributes, at least in part, to increased dissolution rate and/or decreased therapeutic onset time exhibited by amorphous celecoxib and compositions thereof.

Celecoxib Drug Substance of the Invention

In addition to amorphous celecoxib per se, the invention provides a celecoxib drug substance that comprises amorphous celecoxib. At least a detectable amount of amorphous celecoxib is present. Preferably, about 10% to about 100%, more preferably about 25% to about 100%, still more preferably about 60% to about 100%, and even more preferably about 80% to about 100%, by weight of the celecoxib in a celecoxib drug substance of the invention is amorphous. In a particular embodiment, substantially all of the celecoxib is amorphous, i.e., the celecoxib drug substance is substantially phase pure amorphous celecoxib.

A preferred celecoxib drug substance is an entirely solid-state substance wherein the fraction, if any, of the celecoxib that is not amorphous, is crystalline. For example, a microparticulate or nanoparticulate celecoxib drug substance of this embodiment can, in addition to an amorphous celecoxib fraction, comprise a fraction of microcrystalline or nanocrystalline celecoxib, though this crystalline fraction is preferably small, for example, less than about 50%, more preferably less than about 25%, and still more preferably less than about 10%, by weight of the total celecoxib present.

In one embodiment, the amount of amorphous celecoxib in a celecoxib drug substance is sufficient to provide increased dissolution rate as measured in a standard in vitro dissolution assay and/or improved bioavailability (e.g., shorter time to reach a threshold therapeutic concentration in blood plasma, greater $C_{max}$ and/or shorter $T_{max}$) as measured in a standard in vivo pharmacokinetic study, compared with an otherwise similar celecoxib drug substance wherein all, or a substantial portion of, the celecoxib is crystalline.

Amorphous celecoxib or a celecoxib drug substance of the invention can be prepared by any suitable process, not limited to processes described herein.

One illustrative process comprises (a) a step of melting solid-state celecoxib, e.g., crystalline celecoxib; and (b) a step of rapidly cooling the resulting melted celecoxib to form a celecoxib drug substance wherein the celecoxib is present, in at least a detectable amount, in amorphous form. This process optionally further comprises (c) a step of grinding the celecoxib drug substance resulting from step (b) to form a drug powder.

Melting step (a) can be performed by any technique known in the art, for example, by heating the celecoxib in an oven at about 150° C. to about 180° C. Cooling step (b) is typically a quench cooling step that can be performed by any suitable method, for example by immersing a container holding the melted celecoxib in liquid nitrogen. The optional grinding step (c) can be performed by any suitable method, for example by grinding in a mortar and pestle or by grinding in a mill, for example a media mill.

A celecoxib drug substance or drug powder prepared according to the above process or any other process can be administered orally, rectally or parenterally without further formulation, or in simple suspension in water or another pharmaceutically acceptable liquid. Alternatively, the celecoxib drug substance or drug powder can be directly filled into capsules for oral administration. Preferably, however, the celecoxib drug substance or drug powder is subjected to further processing, typically with one or more excipients, to prepare a pharmaceutical composition, for example an oral dosage form, as described hereinbelow.

Celecoxib-crystallization Inhibitor Composites

In a presently preferred embodiment of the invention there is provided a celecoxib-crystallization inhibitor composite comprising particles of amorphous celecoxib or a celecoxib drug substance having at least a detectable amount of amorphous celecoxib, in intimate association with one or more crystallization inhibitors. An "intimate association" in the present context includes, for example, celecoxib admixed with the crystallization inhibitor, celecoxib embedded or incorporated in the crystallization inhibitor, celecoxib forming a coating on particles of the crystallization inhibitor or vice versa, and a substantially homogeneous dispersion of celecoxib throughout the crystallization inhibitor. The term "substantially homogeneous" herein with reference to a composite or pharmaceutical composition that comprises multiple components means that the components are sufficiently mixed such that individual components are not present as discrete layers and do not form concentration gradients within the composition.

A celecoxib-crystallization inhibitor composite of this embodiment preferably comprises about 1% to about 95%, preferably about 10% to about 90%, more preferably about 25% to about 85%, and still more preferably about 30% to about 80%, by weight, of celecoxib. As indicated above, celecoxib in such a composite exists, at least in a detectable amount, in amorphous form. Preferably, about 10% to about 100%, more preferably about 50% to about 100%, and still more preferably about 75% to about 100%, by weight of the total celecoxib in the composite is amorphous celecoxib.

In composites of this embodiment, a fraction of the celecoxib can be present as microcrystalline or nanocrystalline celecoxib, though this fraction is preferably small, for example less than about 50%, more preferably less than about 25%, and still more preferably less than about 10%, by weight of the total celecoxib in the composite.

Crystallization inhibitors include any material which substantially reduces conversion of amorphous celecoxib to crystalline celecoxib, for example, polymers, carbohydrates, lipids, etc. The term "substantially" with respect to reducing such conversion includes completely inhibiting, preventing, slowing, delaying, decreasing or restricting crystallization of celecoxib to a measurable degree. It will be understood that both selection of crystallization inhibitor(s) and the amount of crystallization inhibitor(s) used in a composite of the invention influences stability of amorphous celecoxib therein.

Crystallization inhibitors are preferably polymers, more preferably polymers of low solubility in water. Still more preferably, such polymers are substantially non-crosslinked.

Non-limiting examples of suitable polymers that can be used as crystallization inhibitors include, either alone or in combination, polyvinylpyrrolidone (PVP or povidone, e.g., Kollidon™ CLM of BASF), hydroxypropylmethylcellulose (HPMC, e.g., Methocel™ E5 Premium), HPMC phthalate, ethylcellulose, hydroxyethylcellulose, sodium carboxymethylcellulose (carmellose sodium), calcium carboxymethylcellulose, dextran, acacia, starches such as sodium starch glycolate (SSG, e.g., Explotab™ R of Mendell), β-cyclodextrin (e.g., Kleptose™ 4PC of Roquette), block copolymers of ethylene oxide and propylene oxide (e.g., Pluronic™ F-68 and F-108), polyvinyl alcohol and polyethylene glycol (PEG). Povidone and HPMC are preferred polymers for use as crystallization inhibitors and form celecoxib-polymer composites of the invention.

HPMCs vary in the chain length of their cellulosic backbone and consequently in their viscosity as measured for example at a 2% by weight concentration in water. HPMC used in celecoxib-polymer composites of the invention should have a viscosity, 2% in water, of about 100 to about 100,000 cP, preferably about 1000 to about 15,000 cP, for example about 4000 cP. Molecular weight of HPMC used in celecoxib-polymer composites of the invention is preferably greater than about 10,000 but preferably not greater than about 1,500,000, more preferably not greater than about 1,000,000, still more preferably not greater than about 500,000, and even more preferably not greater than about 150,000.

HPMCs also vary in the relative degree of substitution of available hydroxyl groups on the cellulosic backbone by methoxy and hydroxypropoxy groups. With increasing hydroxypropoxy substitution, the resulting HPMC becomes more hydrophilic in nature. It is preferred in celecoxib-HPMC composites of the present invention to use HPMC having about 15% to about 35%, preferably about 19% to about 32%, and more preferably about 22% to about 30%, methoxy substitution, and having about 3% to about 15%, preferably about 4% to about 12%, and more preferably about 7% to about 12%, hydroxypropoxy substitution.

HPMCs which can be used in the present invention are illustratively available under the brand names Methocel™ of Dow Chemical Co. and Metolose™ of Shin-Etsu Chemical Co. Examples of particularly suitable HPMCs having medium viscosity include Methocel™ E4M and Methocel™

K4M, both of which have a viscosity, 2% in water, of about 4000 cP. Examples of HPMCs having higher viscosity include Methocel™ E10M, Methocel™ K15M and Methocel™ K100M, which have viscosities, 2% in water, of 10,000 cP, 15,000 cP and 100,000 cP respectively.

Preferred povidones used in celecoxib-polymer composites of the invention have a molecular weight of about 2,500 to about 3,000,000, preferably about 8,000 to about 1,000,000, and more preferably about 10,000 to about 400,000, for example, about 50,000. Preferably, povidone used in celecoxib-polymer composites have a dynamic viscosity, 10% in water at 20° C., of about 1.3 to about 700, preferably about 1.5 to about 300, and more preferably about 3.5 to about 8.5 mPas.

In celecoxib-crystallization inhibitor composites, for example celecoxib-polymer composites, of the invention, the amount of crystallization inhibitor is preferably sufficient such when maintained in an open dish at ambient temperature for a period of 7 days, transformation of amorphous celecoxib to crystalline celecoxib is no greater than about 50%, preferably no greater than about 25%, and more preferably no greater than about 10%, by weight of all celecoxib in the composite.

Typically, depending on the particular polymer(s) used, one or more polymers are present in a contemplated celecoxib-polymer composite in a total amount of about 10% to about 80%, preferably about 15% to about 75%, and more preferably about 25% to about 65%, by weight. Preferably, the weight ratio of celecoxib to polymer is about 1:1000 to about 10:1, more preferably about 1:10 to about 5:1, and still more preferably about 1:2 to about 2.5:1.

A celecoxib-crystallization inhibitor composite of the invention can be prepared by any suitable process, not limited to processes described herein.

One illustrative process comprises (a) a step of dissolving celecoxib and one or more crystallization inhibitors in a solvent liquid to form a solution; and (b) a step of drying the solution to form a celecoxib-crystallization inhibitor composite wherein the celecoxib and the crystallization inhibitor are in intimate association and wherein at least a detectable fraction of the celecoxib is in amorphous form. Optionally, this process can further comprise a step (c) of grinding the celecoxib-crystallization inhibitor composite to form a celecoxib-crystallization inhibitor composite powder.

Suitable solvent liquids which can be used to prepare a celecoxib-crystallization inhibitor composite, for example a celecoxib-polymer composite, can comprise any pharmaceutically acceptable solvent in which celecoxib can be dissolved. Heat and stirring can be used to facilitate drug dissolution in the solvent liquid. The solvent liquid can also comprise a non-solvent fraction, for example, water. Non-limiting examples of suitable solvents that may be used in solvent liquids of the invention include, for example, water-alcohol mixtures, methanol, ethanol, isopropanol, higher alcohols, propylene glycol, ethyl caprylate, propylene glycol laurate, PEG, diethyl glycol monoethyl ether (DGME), tetraethylene glycol dimethyl ether, triethylene glycol monoethyl ether, polysorbate 80, etc. Ethanol and isopropanol are preferred solvents.

It has surprisingly been found that use of isopropanol as a solvent permits a relatively high loading of celecoxib and polymer in the solution to be dried; accordingly isopropanol is presently an especially preferred solvent.

The drying step (b) can be performed by any suitable means, for example, by evaporation, lyophilization, conventional heating (e.g., in an oven), spray drying, etc. Spray drying is a preferred method of drying. Any suitable spray drying method known in the art can be employed. Generally, spray drying is a process by which a solution comprising dissolved drug and crystallization inhibitor is rapidly sprayed over a current of warm air, resulting in formation of dry powder.

The optional grinding step (c) can be performed by any suitable method, for example by grinding in a mortar and pestle or by grinding in a mill, for example a media mill.

A celecoxib-crystallization inhibitor composite, for example a celecoxib-polymer composite or a powder thereof, prepared according to the above process or any other process, can be administered orally, rectally or parenterally without further formulation, or in simple suspension in water or another pharmaceutically acceptable liquid. Alternatively, the composite or powder thereof can be directly filled into capsules for oral administration. Preferably, however, the composite or powder thereof is subjected to further processing, typically with one or more additional excipients, to prepare a pharmaceutical composition, for example an oral dosage form, as described hereinbelow.

Pharmaceutical Compositions

Amorphous celecoxib, a celecoxib drug substance or a celecoxib-crystallization inhibitor composite as provided herein can be further formulated together with one or more pharmaceutically acceptable excipients to produce a pharmaceutical composition. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients include, by way of illustration and not limitation, diluents, disintegrants, binding agents, adhesives, wetting agents, lubricants, glidants, crystallization inhibitors, surface modifying agents, substances added to mask or counteract a disagreeable taste or odor, flavors, dyes, fragrances, and substances added to improve appearance of the composition.

Excipients employed in compositions of the invention can be solids, semi-solids, liquids or combinations thereof. Compositions of the invention containing excipients can be prepared by any known technique of pharmacy that comprises admixing an excipient with a drug or therapeutic agent. A composition of the invention contains a desired amount of celecoxib per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended for parenteral administration, it can be in the form, for example, of a suspension. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after a drying step) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the celecoxib in close association with water, a condition that is believed to improve bioavailability of the composition.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium, calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of the composition.

According to a particularly preferred embodiment of the invention, an effervescent agent, present in a solid dosage form in an amount less than that effective to promote disintegration of the dosage form, provides improved dispersion of the celecoxib in an aqueous medium. Without being bound by theory, it is believed that the effervescent agent is effective to accelerate dispersion of celecoxib from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents useful in the invention include citric acid, tartaric acid, malic acid, faimaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Solid dosage forms of the invention can be prepared by any suitable process, not limited to processes described herein.

An illustrative process comprises (a) a step of blending amorphous celecoxib, a celecoxib drug substance, or a celecoxib-crystallization inhibitor composite of the invention with one or more excipients to form a blend, and (b) a step of tableting or encapsulating the blend to form tablets or capsules respectively.

In a preferred process, solid dosage forms are prepared by a process comprising (a) a step of blending amorphous celecoxib, a celecoxib drug substance, or a celecoxib-crystallization inhibitor composite of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a wet granulation step followed by a step of drying the resulting granulate prior to tableting or encapsulating. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the amorphous celecoxib, celecoxib drug substance or celecoxib-crystallization inhibitor composite is suspended with one or more excipients in one or more sprayable liquids, preferably a non-aqueous sprayable liquid, and then is rapidly spray dried over a current of warm air. This spray drying process for preparing a pharmaceutical composition can be performed in addition to any spray drying step used in preparation of a celecoxib-crystallization inhibitor composite as described hereinabove, but formation of the celecoxib-crystallization inhibitor composite is preferably combined with a spray drying step for preparation of the pharmaceutical composition.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Any tablet hardness convenient with respect to handling, manufacture, storage and ingestion can be employed. For example, for 100 mg celecoxib tablets, hardness is preferably at least about 4 kP, more preferably at least about 5 kP, and still more preferably at least about 6 kP. For 200 mg celecoxib tablets, hardness is preferably at least about 7 kP, more preferably at least about 9 kP, and still more preferably at least about 11 kP. The material to be tableted, however, should not be compressed to such a degree that there is subsequent difficulty in achieving hydration when exposed to gastric fluid.

Tablet friability preferably is less than about 1.0%, more preferably less than 0.8%, and still more preferably less than about 0.5% in a standard test.

Celecoxib Dosage

Celecoxib dosage forms of the invention preferably comprise celecoxib in a daily dosage amount of about 10 mg to about 1000 mg, more preferably about 25 mg to about 400 mg, and most preferably about 50 mg to about 200 mg.

Compositions of the invention comprise one or more orally deliverable dose units. Each dose unit comprises celecoxib in a therapeutically effective amount that is preferably about 10 mg to about 1000 mg. The term "dose unit" herein means a portion of a pharmaceutical composition that contains an amount of a therapeutic or prophylactic agent, in the present case celecoxib, suitable for a single oral administration to provide a therapeutic effect. Typically one dose unit, or a small plurality (up to about 4) of dose units, in a single administration provides a dose comprising a sufficient amount of the agent to result in the desired effect. Administration of such doses can be repeated as required, typically at a dosage frequency of 1 to about 4 times per day.

It will be understood that a therapeutically effective amount of celecoxib for a subject is dependent inter alia on the body weight of the subject. A "subject" herein to which a therapeutic agent or composition thereof can be administered includes a human patient of either sex and of any age, and also includes any nonhuman animal, particularly a warm-blooded animal, more particularly a domestic or companion animal, illustratively a cat, dog or horse. When the subject is a child or a small animal (e.g., a dog), for example, an amount of celecoxib relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib are likely to require dose units containing a relatively greater amount of celecoxib.

Typical dose units in a composition of the invention contain about 10, 20, 25, 37.5, 50, 75, 100, 125, 150, 175, 200, 250, 300, 350 or 400 mg of celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg.

A dose unit containing a particular amount of celecoxib can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

The term "oral administration" herein includes any form of delivery of a therapeutic agent or a composition thereof to a subject wherein the agent or composition is placed in the mouth of the subject, whether or not the agent or composition is immediately swallowed. Thus "oral administration" includes buccal and sublingual as well as esophageal administration. Absorption of the agent can occur in any part or parts of the gastrointestinal tract including the mouth, esophagus, stomach, duodenum, ileum and colon. The term "orally deliverable" herein means suitable for oral administration.

Utility of Compositions of the Invention

Compositions of the invention are useful in treatment and prevention of a very wide range of disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Contemplated compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic diseases, such as retinitis, conjunctivitis, retinopathies, uveitis, ocular photophobia, and of acute injury to the eye tissue.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in patients at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention.

Besides being useful for human treatment, compositions of the invention are useful for veterinary treatment of companion animals, exotic animals, farm animals, and the like, particularly mammals. More particularly, compositions of the invention are useful for treatment of COX-2 mediated disorders in horses, dogs and cats.

Method of Treatment

The present invention is further directed to a therapeutic method of treating a condition or disorder where treatment with a COX-2 inhibitory drug is indicated, the method comprising oral administration of a composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

The present compositions can be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis (acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, β-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsahnide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index*, 12th Edition, Therapeutic Category and Biological Activity Index, ed. S. Budavari (1996), pp. Ther-2 to Ther-3 and Ther-12 (Analgesic (Dental), Analgesic (Narcotic), Analgesic (Non-narcotic), Anti-inflammatory (Nonsteroidal)).

Particularly preferred combination therapies comprise use of a composition of the invention with an opioid compound, more particularly where the opioid compound is codeine, meperidine, morphine or a derivative thereof.

A celecoxib composition of the invention can also be administered in combination with a second selective COX-2 inhibitory drug, for example valdecoxib, rofecoxib, etc.

The compound to be administered in combination with celecoxib can be formulated separately from the celecoxib or co-formulated with the celecoxib in a composition of the invention. Where celecoxib is co-formulated with a second drug, for example an opioid drug, the second drug can be formulated in immediate-release, rapid-onset, sustained-release or dual-release form.

EXAMPLES

The following examples illustrate aspects of the present invention but are not to be construed as limitations.

Example 1

A celecoxib drug substance C1 and celecoxib-polymer composites C3 and C4 were prepared by the following spray drying process. Celecoxib in crystalline form (a celecoxib drug substance C2 of prior art) was added to a solvent, with stirring at a temperature of 70–75° C., to prepare solutions S1, S3 and S4 having the composition shown in Table 1,. Solutions S1 and S4 were prepared in 95% ethanol. Solution S3 was prepared in 70% isopropanol.

TABLE 1

| Composition (mg/ml) of solutions S1, S3 and S4. | | | |
|---|---|---|---|
| Component | S1 | S3 | S4 |
| Celecoxib | 30 | 100 | 30 |
| HPMC | — | 50 | — |
| Povidone | — | — | 15 |

Each of solutions S1, S3 and S4 was spray dried individually at room temperature using a Yamato GB-21 spray dryer to form powders C1, C3 and C4, respectively, under the following conditions: (a) liquid flow rate of 10 ml/min; (b) inlet air temperature of 115° C.; (c) outlet air temperature of 75° C., and (d) drying airflow of 3.75 TMF. Powders C3 and C4 are celecoxib-polymer composites of the invention, each comprising 67% celecoxib and 33% polymer.

Example 2

A celecoxib drug substance C10 was prepared by the following melt/quench cool process.

Approximately 5 g of crystalline celecoxib (the prior art celecoxib drug substance C2) was weighed into a metal foil tray and placed in an oven at 180° C. for 5 minutes to melt the celecoxib. This was then quench cooled by immersing the foil tray containing the melted celecoxib in liquid nitrogen, resulting in the formation of celecoxib drug substance C10 of the present invention. This drug substance could be gently ground by mortar and pestle to produce a celecoxib drug substance powder.

Example 3

Powder X-ray diffraction (PXRD) analysis was used to determine the relative crystalline and amorphous celecoxib content of celecoxib drug substance C1 and celecoxib-polymer composites C3 and C4 as prepared in Example 1, by comparison with crystalline celecoxib drug substance C2. Data were collected using a Scintag Advanced Diffraction System operating under Scintag DMS/NT software. This system uses a peltier cooled solid state detector and a copper X-ray source maintained at 45 kV and 40 mA to provide $CuK\alpha_1$ emission at 1.5406 Å. The beam aperture was controlled using tube divergence and anti-scatter slits of 2 and 4 mm respectively, while the detector anti-scatter and receiving slits were set at 0.5 and 0.3 mm respectively. Data were collected from 2° to 35° two-theta (2θ) using a scan step of 0.03°/point and a one second/point integration time. The samples were prepared using Scintag round top-loading stainless steel sample cups, and were fitted with 12 mm diameter aluminum inserts to accommodate small sample volumes.

Figure 2:
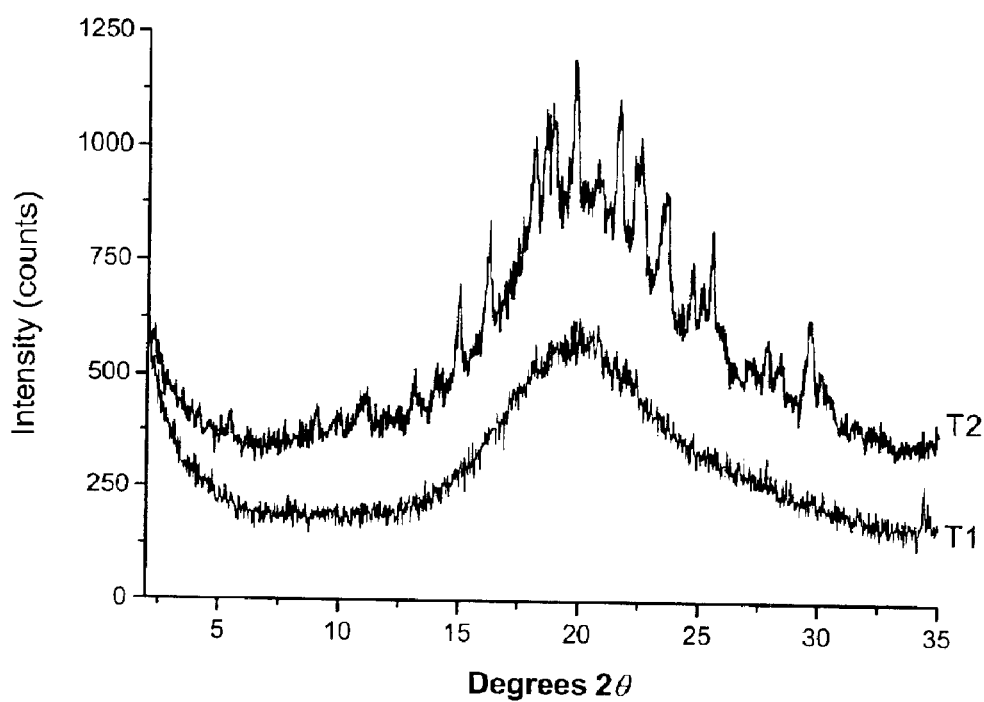
FIG. 2 shows powder X-ray diffraction profiles of a celecoxib-polymer composite C3 of the invention immediately after preparation (T1) and following storage for 2 weeks at 40° C. and 75% relative humidity (T2).
Figure 3:
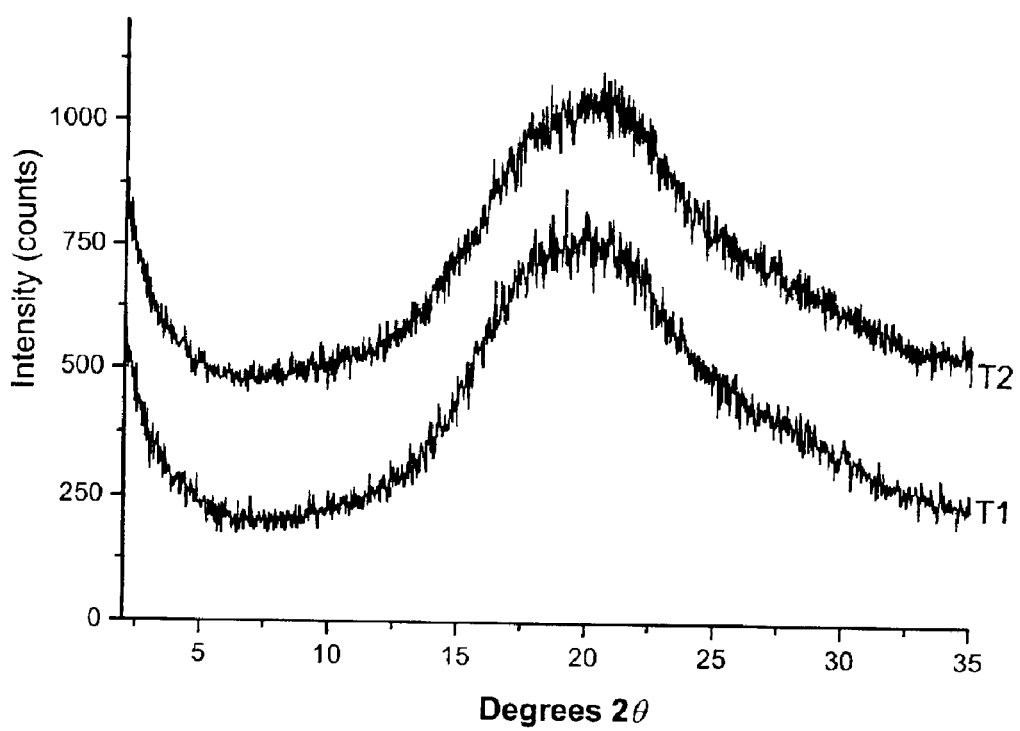
FIG. 3 shows powder X-ray diffraction profiles of a celecoxib-polymer composite C4 of the invention immediately after preparation (T1) and following storage for 2 weeks at 40° C. and 75% relative humidity (T2).

The results of the PXRD analyses are shown as bands in FIGS. 1–3. The appearance of larger, spiked peaks on a band indicates crystallinity whereas compressed peaks are indicative of amorphous material.

FIG. 1 shows that celecoxib alone (with no polymer) spray dried from an ethanol solution (C1) produced a strong crystalline signal similar to that of a crystalline celecoxib control (C2). If there is an amorphous component in celecoxib drug substance C1 it is a minor component.

FIG. 2 shows that when celecoxib was spray dried with HPMC (2:1 ratio by weight), the resulting celecoxib-polymer composite C3 was initially (at time T1) non-crystalline, i.e., the celecoxib in this composite was substantially phase pure amorphous celecoxib. When analysis was conducted on a sample that had been stored for two weeks at 40° C. and 75% relative humidity (at time T2), some recrystallization had occurred, as indicated by presence of crystalline peaks.

FIG. 3 shows that when celecoxib was spray dried with povidone (2:1 ratio by weight) the resulting celecoxib-polymer composite C4 was initially (at time T1) non-crystalline, i.e., the celecoxib in this composite was substantially phase pure amorphous celecoxib. When analysis was conducted on a sample that had been stored for two weeks at 40° C. and 75% relative humidity (at time T2), essentially no recrystallization had occurred, as indicated by absence of crystalline peaks.

Example 4

Differential scanning calorimetry (DSC) was used to determine relative crystalline and amorphous celecoxib content of celecoxib drug substance C1 and celecoxib-polymer composites C3 and C4 as prepared in Example 1. DSC was performed using a TA Instruments DSC 2920 differential scanning calorimeter with parameters set as follows: (a) temperature range of 50–200° C.; (b) heating rate of 2° C./min, modulating ±0.5° C. every 30 sec; (c) sample size of 3 mg; (d) hermetically sealed aluminum pans.

Figure 4:
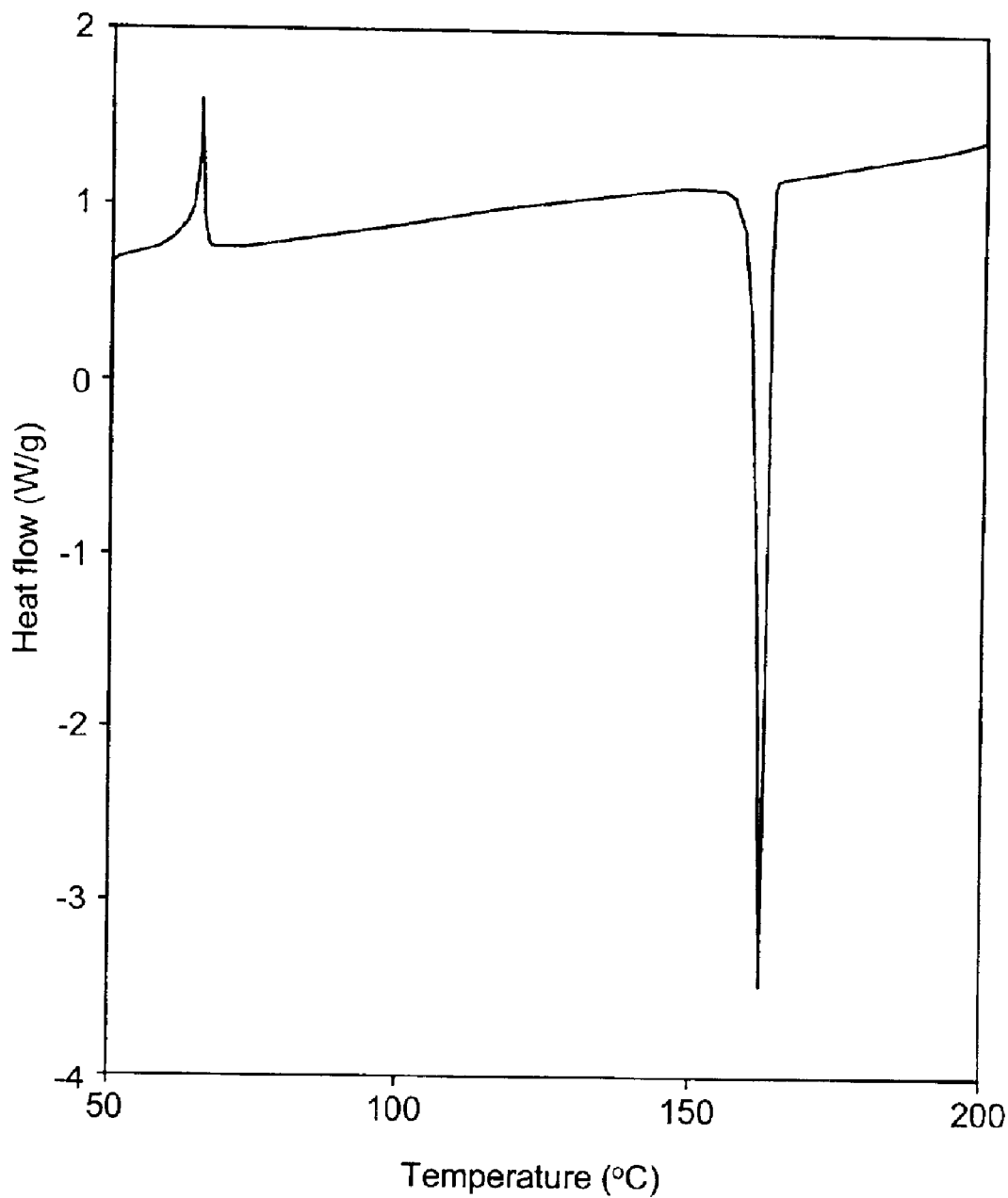
FIG. 4 shows a differential scanning calorimetry (DSC) thermogram of a celecoxib drug substance C1 comprising no polymer.
Figure 5:
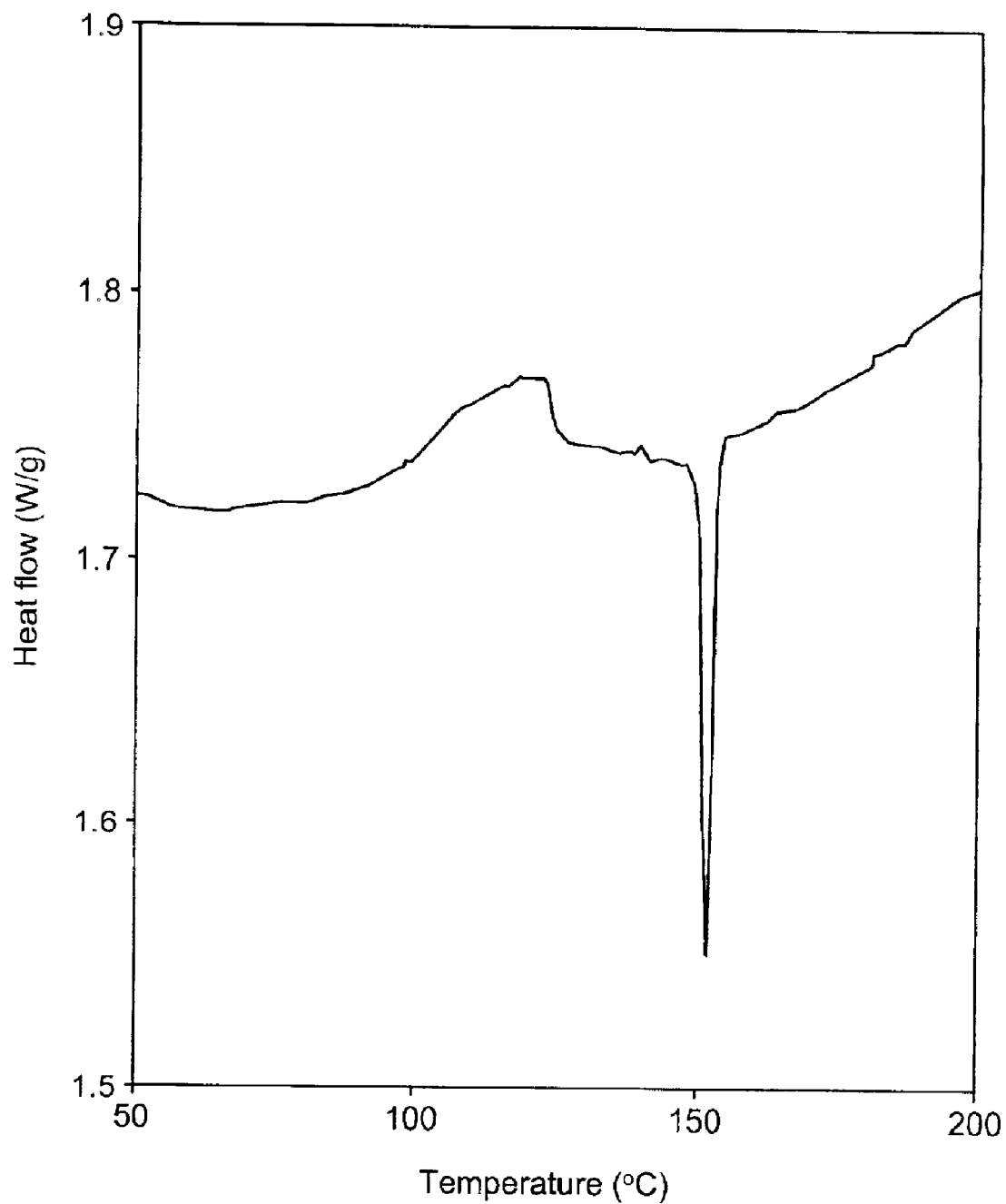
FIG. 5 shows a DSC thermogram of a celecoxib-polymer composite C3 of the invention wherein the polymer is hydroxypropylmethylcellulose.
Figure 6:
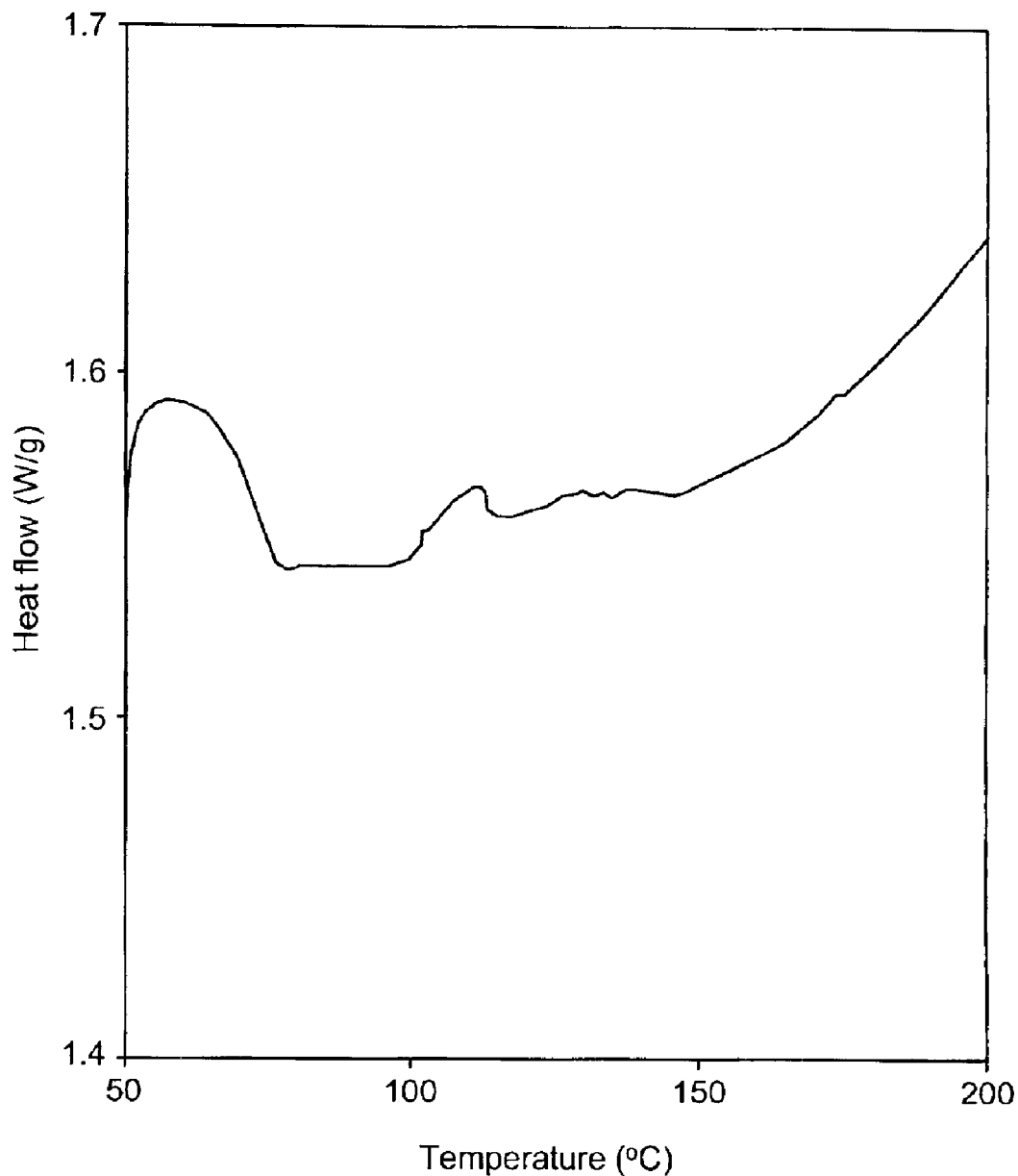
FIG. 6 shows a DSC thermogram of a celecoxib-polymer composite C4 of the invention wherein the polymer is polyvinylpyrrolidone.

FIGS. 4–6 show DSC thermograms for the spray dried powders of Example 1.

FIG. 4 displays a thermogram for celecoxib drug product C1, exhibiting a large melting endotherm at 159.4° C. (onset) with an area of 96.42 J/g. No other transitions are evident. The magnitude of the endotherm suggests that a substantial portion of C1 was crystalline. Any amorphous celecoxib present in the sample was not detectable by this technique.

FIG. 5 displays a thermogram for celecoxib-polymer composite C3 (2:1 celecoxib:HPMC ratio). This material exhibits an apparent glass transition at 122.9° C. (onset), followed by a small melting endotherm at 150.1° C. with an area of 4.379 J/g. The endotherm indicates that most of the celecoxib in C3 is amorphous, but that a small amount of crystalline celecoxib is present.

FIG. 6 displays a thermogram for celecoxib-polymer composite C4 (2:1 celecoxib:povidone ratio). This material exhibits an apparent glass transition at 111.4° C. (onset). No other transitions are evident, indicating that the material is substantially phase pure amorphous celecoxib.

Example 5

DSC was also used to determine relative crystalline and amorphous content of celecoxib drug substance C10 prepared as in Example 2. DSC was performed using a TA Instruments MDSC differential scanning calorimeter at a scan rate of 5° C./min.

A first significant thermal event was observed at about 54° C., representing a glass transition temperature indicative of amorphous celecoxib. An exothermic peak observed at 100–105° C. was consistent with a crystallization event and represents conversion of amorphous celecoxib to a crystalline state. As was shown by the presence of a endothermic peak, the resulting crystalline celecoxib melted at about 165° C.

Example 6

Tablets having the composition shown in Table 2 were prepared from celecoxib-polymer composite C4 by the following procedure. Composite C4, sodium lauryl sulfate and effervescent agents (citric acid and sodium bicarbonate) were admixed and milled for 10 min in a McCrone mill to form a powder mixture. The powder mixture was ground together with lactose, microcrystalline cellulose and sodium starch glycolate using a mortar and pestle to form a ground powder mixture. The ground powder mixture was then compressed using a Carver press to form tablets, which are illustrative of a pharmaceutical composition of the invention.

TABLE 2

Composition of tablets prepared from celecoxib-polymer composite C4

| Component | Amount/tablet (mg) |
| --- | --- |
| Composite C4 | 300 |
| Sodium lauryl sulfate | 3 |
| Citric acid | 15.9 |
| Sodium bicarbonate | 25.2 |
| Lactose | 50 |
| Microcrystalline cellulose | 57 |
| Sodium starch glycolate | 48 |
| Total | 499 |

Example 7

Tablets prepared as described in Example 6 were compared with a crystalline celecoxib capsule in an in vivo bioavailability assay in dogs. In a crossover design, each of six beagle dogs received a 200 mg dose of celecoxib in the form of the tablet composition of Example 6, and then after a washout period, the dogs each received a 200 mg dose of celecoxib in the form of a commercial Celebrex® 200 mg capsule, which contains celecoxib entirely in crystalline form. Blood plasma was collected pre-dose and at 0.25, 0.5, 0.75, 1, 1.5, 2, 3, 5, 8 and 24 hours post-dose. Celecoxib concentrations in plasma were measured using liquid chromatography/mass spectrometry. $C_{max}$, $T_{max}$ and AUC (area under the curve, a measure of total bioavailability) were calculated from the data in accordance with standard procedure in the art. Mean results for all dogs are shown in Table 3.

The tablet of Example 6 prepared from amorphous celecoxib exhibited a significantly greater $C_{max}$ (maximum blood plasma concentration), a comparable $T_{max}$, and a significantly greater AUC than the capsule formulated from crystalline celecoxib. As a measure of relative onset time, the time taken for the tablet of the invention to reach a plasma concentration equal to the $C_{max}$ of the crystalline celecoxib capsule was only 0.5 hour, by comparison with 1.2 hours (the $T_{max}$ for the crystalline celecoxib capsule).

TABLE 3

Bioavailability of the amorphous celecoxib tablet of Example 6 by comparison with a capsule of crystalline celecoxib

|  | Tablet, amorphous | Capsule, crystalline |
|---|---|---|
| $T_{max}$ (h) | 1.4 | 1.2 |
| $C_{max}$ (ng/ml) | 2130 | 1011 |
| AUC (ng/ml*h) | 17900 | 8470 |
| Relative onset time (h) | 0.5 | — |

What is claimed is:

1. Amorphous celecoxib, wherein said amorphous celecoxib exhibits a glass transition measurable by differential scanning calorimetry.

2. A pharmaceutical composition comprising amorphous celecoxib in a total celecoxib dosage amount of about 10 mg to about 1000 mg, and one or more pharmaceutically acceptable excipients, wherein said amorphous celecoxib exhibits a glass transition measurable by differential scanning calorimetry.

3. Amorphous celecoxib as set forth in claim 1 having a $C_{max}$ greater than the $C_{max}$ of crystalline celecoxib.

4. Amorphous celecoxib as set forth in claim 1 having an AUC greater than the AUC of crystalline celecoxib.

* * * * *